(12) United States Patent
Jutamulia et al.

(10) Patent No.: US 8,785,885 B1
(45) Date of Patent: Jul. 22, 2014

(54) FLUORESCENCE IMAGING MODULE

(71) Applicant: OmniVision Technologies, Inc., Santa Clara, CA (US)

(72) Inventors: Suganda Jutamulia, Berkeley, CA (US); Hasan Gadjali, Fremont, CA (US); Junzhao Lei, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 64 days.

(21) Appl. No.: 13/753,887

(22) Filed: Jan. 30, 2013

(51) Int. Cl.
*G01N 21/64* (2006.01)
(52) U.S. Cl.
CPC ............................. *G01N 21/64* (2013.01)
USPC ........................................................ 250/458.1
(58) Field of Classification Search
CPC ............ G01N 21/6458; G01N 21/64; G01N 2021/6463; G01N 2021/6478; G02B 21/16
USPC ........................................................ 250/458.1
See application file for complete search history.

(56) References Cited

U.S. PATENT DOCUMENTS

| | | | |
|---|---|---|---|
| 6,867,860 B2 * | 3/2005 | Tanaami et al. | 356/318 |
| 7,321,791 B2 | 1/2008 | Levenson et al. | |
| 8,040,515 B2 * | 10/2011 | Sonehara et al. | 356/417 |
| 2005/0057798 A1 * | 3/2005 | Osborne et al. | 359/368 |
| 2005/0110998 A1 * | 5/2005 | Lin et al. | 356/417 |
| 2008/0310016 A1 * | 12/2008 | Karasawa et al. | 359/383 |
| 2010/0294947 A1 * | 11/2010 | Oda et al. | 250/458.1 |
| 2011/0096967 A1 * | 4/2011 | Oda et al. | 382/128 |

OTHER PUBLICATIONS

G. Themelis et al., "Real-time intraoperative fluorescence imaging system using light-absorption correction," Journal of Biomedical Optics 14(6), 064012 (Nov./Dec. 2009).

* cited by examiner

*Primary Examiner* — Marcus Taningco
(74) *Attorney, Agent, or Firm* — Blakely Sokoloff Taylor & Zafman LLP

(57) ABSTRACT

A fluorescence imaging module includes an image sensor and a lens disposed between a fluorescence sample and the image sensor to focus a fluorescence image of the fluorescence sample onto the image sensor. The fluorescence sample is to be positioned an object distance away from the lens. The lens is positioned an image distance away from the image sensor. The image distance is greater than the object distance. An illuminating device is disposed between the fluorescence sample and the lens. The illuminating device includes a light source and an optical element. The light source is adapted to emit light in a first direction towards the optical element. The optical element is optically coupled to receive the light and redirect the light in a second direction towards the fluorescence sample to illuminate the fluorescence sample.

26 Claims, 8 Drawing Sheets

PRIOR ART FIG. 1

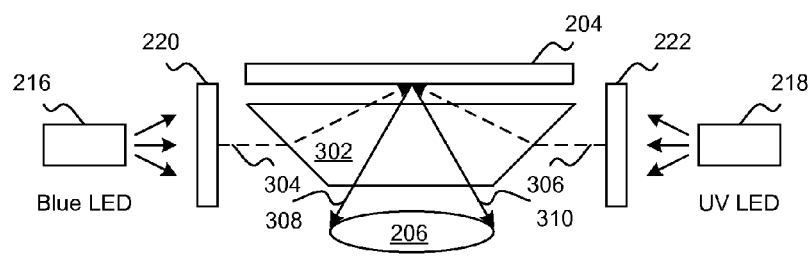
FIG. 3
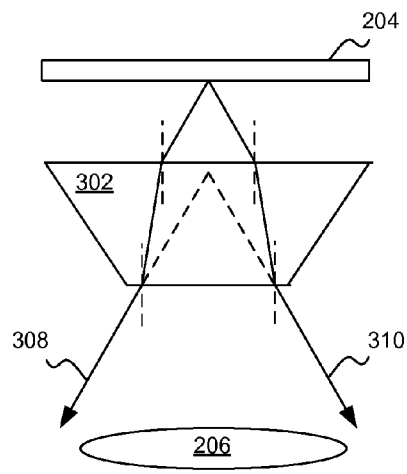
FIG. 4
FIG. 5
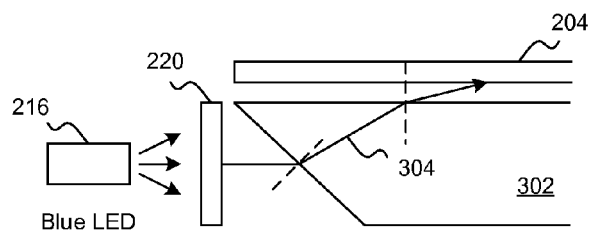

FLUORESCENCE IMAGING MODULE

BACKGROUND INFORMATION

1. Field of the Disclosure

The present invention relates generally to a fluorescence imaging module, and more specifically to a fluorescence imaging module having an illuminating device capable of bending illuminating light toward the fluorescence sample.

2. Background

The technique of fluorescence microscopy has become a valuable tool in biology and biomedicine due to attributes that are not readily available in traditional optical microscopy. A fluorescence object emits fluorescence emission light after the absorption of excitation light. A variety of specimens exhibit autofluorescence when they are illuminated by excitation light. For non-autoflourescence specimens, the application of fluorophores has made it possible to identify cells and sub-microscopic cellular components with a high degree of specificity. The added fluorophores are excited by illuminating light having an excitation wavelength and emit light having an emission wavelength, which is longer than the excitation wavelength. Fluorophores are stains that attach themselves to target structures. The widespread growth in the utilization of fluorescence microscopy is closely linked to the development of new synthetic and naturally occurring fluorophores with known profiles of excitation and emission, along with well-understood biological targets.

An example of a fluorescence microscope 100 is depicted in FIG. 1. A white light emitting diode (LED) 102 illuminates a fluorescence sample 104 on a microscope slide. A microscope objective 106 in combination with a tube lens (eyepiece) 108 acquires an image of sample 104 on an image sensor 110. An ultraviolet LED 118 and a blue LED 116 are used to illuminate sample 104. The illuminating light having the ultraviolet and blue wavelengths excites sample 104 such that sample 104 emits fluorescence light. Sample 104 may exhibit autofluorescence or may have been stained with fluorophores. Excitation filters 122 and 120 filter the excitation light emitted by ultraviolet LED 118 and blue LED 116, respectively. The light beams after passing excitation filters 120 and 122 are combined by a first dichroic minor 114. The combined excitation light beams from ultraviolet LED 118 and blue LED 116 are reflected by a second dichroic minor 112 to illuminate sample 104. The emitted fluorescence light from sample 104 is transmitted through second dichroic mirror 112, passes through an emission filter 124, and forms the image of fluorescence sample 104 on camera 110.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 3 shows an illuminating device comprising a truncated pyramid in accordance with the teachings of the present invention.

FIG. 4 illustrates light passing though two parallel planes of truncated pyramid in accordance with the teachings of the present invention.

FIG. 5 illustrates light that is bent by truncated pyramid in accordance with the teachings of the present invention.

Figure 1:
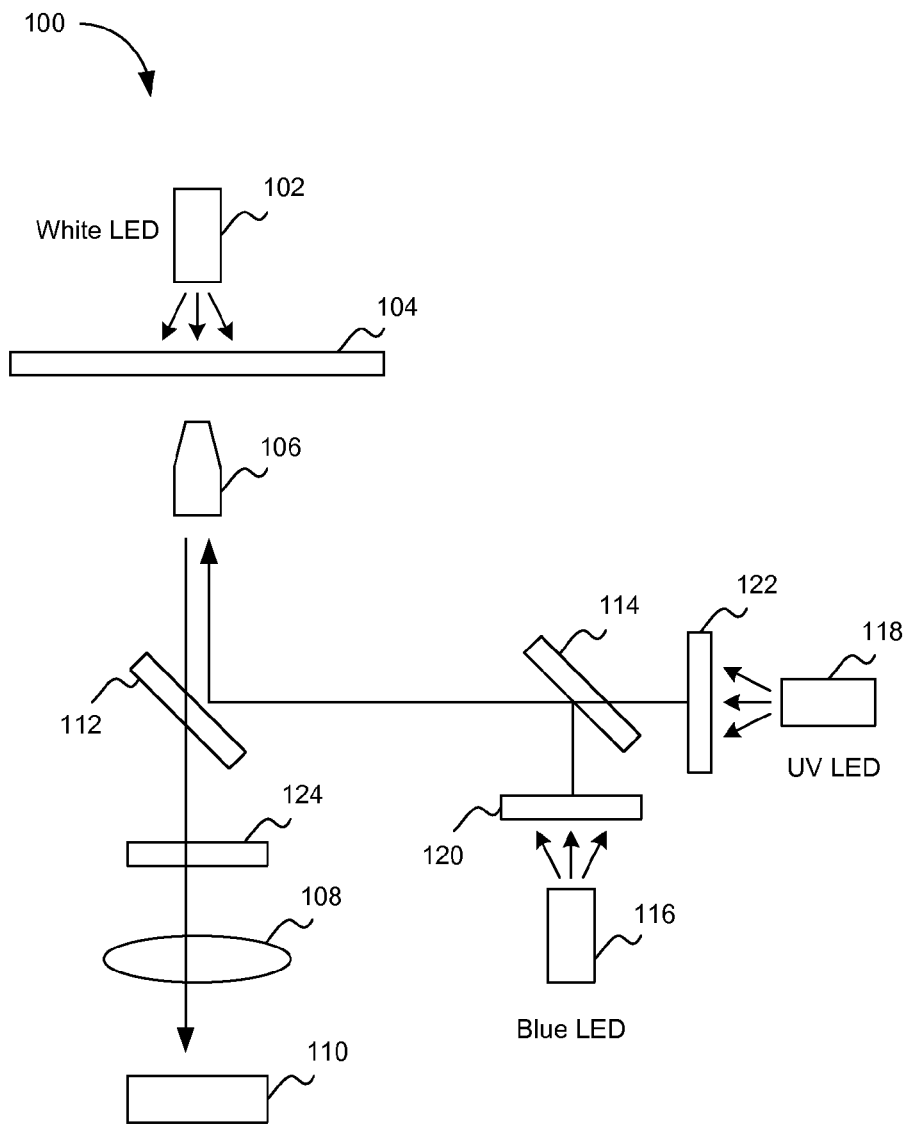
FIG. 1 shows an example fluorescence microscope.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or subcombinations in one or more embodiments or examples. Particular features, structures or characteristics may be included in an integrated circuit, an electronic circuit, a combinational logic circuit, or other suitable components that provide the described functionality. In addition, it is appreciated that the figures provided herewith are for explanation purposes to persons ordinarily skilled in the art and that the drawings are not necessarily drawn to scale.

As summarized above, the fluorescence microscope 100 depicted in FIG. 1 includes several dichroic mirrors 112 and 114. Dichroic mirrors are relatively expensive. As will be described below, an example reduced-cost fluorescence imaging module using no dichroic minors or a reduced number of dichroic mirrors is provided in accordance with the teachings of the present invention.

In addition, it is noted that the microscope 100 depicted in FIG. 1 includes an objective lens, which therefore contributes to the overall length of fluorescence microscope 100. In particular, the distance from the focus of the microscope objective 106 to the focus of the tube lens (eyepiece) 108 in a microscope is standardized at 160 mm, which is known as the tube length. This makes the total length from the microscope objective 106 to the tube lens 108 (f1+160+f2) mm, where f1 and f2 are focal lengths of the microscope objective 106 and tube lens 108, respectively. As will be described below, an example reduced-cost fluorescence imaging module having a shorter total length than microscope 100 is disclosed in accordance with the teachings of the present invention.

In the construction of an example fluorescence imaging module in accordance with the teachings of the present invention, a desired magnification M may be considered according to the following ratio:

$$M = P_{SIZE}/F_{SIZE}, \quad (1)$$

where M is the magnification, $P_{SIZE}$ is the pixel size of an image sensor, and $F_{SIZE}$ is the desired resolution of the smallest feature of the sample. For instance, assume in one example that the image sensor has a pixel size of 1.4 μm and that the desired resolution of the smallest feature of the sample is 0.2 μm. Accordingly, the desired magnification M is the pixel size divided by the smallest feature size, which is 1.4 μm/0.2 μm=7.

Figure 2:
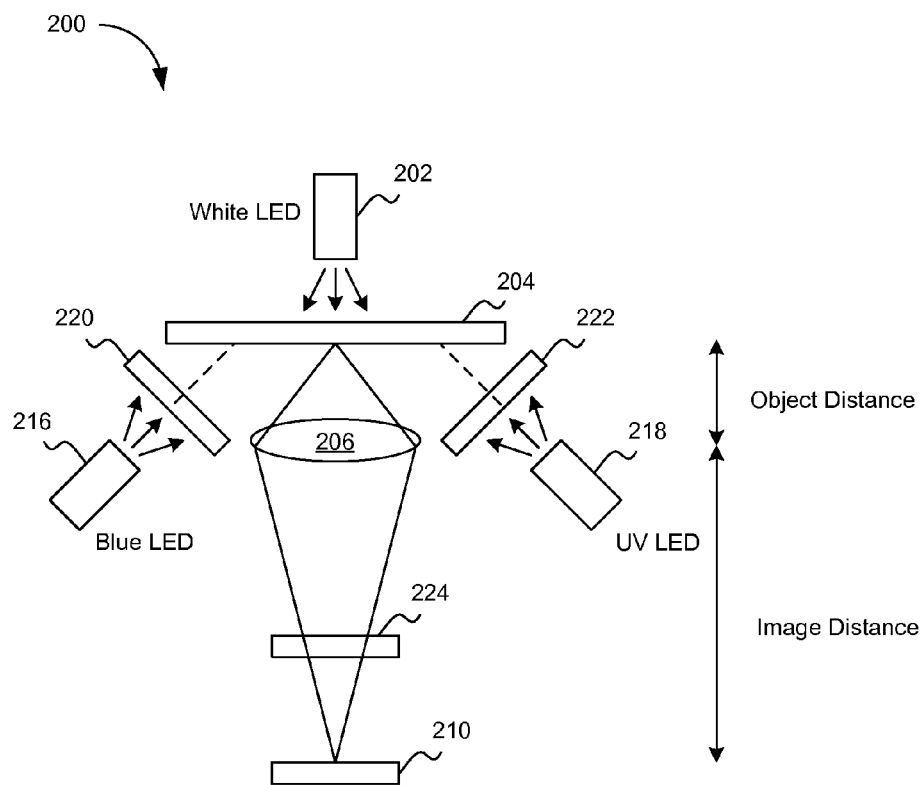
FIG. 2 shows an example fluorescence imaging module in accordance with the teachings of the present invention.

FIG. 2 illustrates one example of a fluorescence imaging module 200 in accordance with the teachings of the present invention. In the depicted example, a white LED 202 illuminates a fluorescence sample 204 on a microscope slide. A lens or lens system 206 acquires an image of fluorescence sample 204 on an image sensor 210. In the illustrated example, an ultraviolet LED 218 and a blue LED 216 are used to directly illuminate fluorescence sample 204. The ultraviolet and blue wavelengths of the light used to illuminate fluorescence sample 204 from ultraviolet LED 218 and blue LED 216 excites fluorescence sample 204 such that fluorescence sample 204 emits fluorescence light.

In one example, fluorescence sample 204 exhibits autofluorescence. In another example, fluorescence sample 204 is stained with fluorophores. In one example, excitation filters 222 and 220 are optionally included to filter the excitation light emitted by ultraviolet LED 218 and blue LED 216, respectively. The emitted fluorescence light from fluorescence sample 204 is transmitted through an emission filter 224, and forms the fluorescence image of fluorescence sample 204 on image sensor 210. It is appreciated that in fluorescence imaging module 200, no dichroic minor is included in accordance with the teachings of the present invention.

To provide the desired magnification M, which is assumed to be M=7 in the described example, the ratio of the image distance to the object distance must be 7 (or M). Using the lens equation:

$$1/o + 1/i = 1/f, \quad (2)$$

where o is the object distance, i is the image distance, and f is the focal length of lens, we can calculate the image distance, the focal length of lens, and the total length, which is the sum of the object distance and the image distance, as functions of the object distance that meet the required magnification, e.g., 7, as shown in Table 1 below.

TABLE 1

| Magnification | Object Distance | Image Distance | Focal Length | Total Length (Object Distance + Image Distance) |
|---|---|---|---|---|
| 7 | 5 mm | 35 mm | 4.375 mm | 40 mm |
| 7 | 10 mm | 70 mm | 8.75 mm | 80 mm |
| 7 | 15 mm | 105 mm | 13.125 mm | 120 mm |
| 7 | 20 mm | 140 mm | 17.5 mm | 160 mm |
| 7 | 25 mm | 175 mm | 21.875 mm | 200 mm |
| 7 | 30 mm | 210 mm | 26.25 mm | 240 mm |

Fluorescence imaging module 200 of FIG. 2 is different from a regular camera, such as for example when the regular camera is used for taking picture of an object that is far from the camera. For instance, in the regular camera, the magnification M is less than unity and the image distance is less than the object distance. Since the object is far away from the camera, the image of the object is often formed on the focal plane of the lens of camera.

However, in fluorescence imaging module 200 of FIG. 2, the magnification is greater than unity and the image distance is greater than the object distance. In particular, the distance between fluorescence sample 204 and lens 206 is defined as the object distance. The distance between lens 206 and image sensor 210 is defined as the image distance. The magnification is the ratio of the image distance to the object distance, which can be determined according to the following ratio:

$$M = i/o \quad (3)$$

where M is the magnification, o is the object distance, and i is the image distance.

For a desired magnification equal to M, a table may be obtained following the same procedure of Table 1 above, except that the ratio of the image distance i to the object distance o is M instead of 7. From Table 1, it is seen that fluorescence imaging module 200 of FIG. 2 may be made shorter that fluorescence microscope 100 of FIG. 1, which includes microscope objective 106 as summarized above. In particular the total distance in fluorescence imaging module 200 of FIG. 2 of the image sensor 210 to the fluorescence sample 204 is substantially equal to the sum of the object distance (o) and the image distance (i).

It is noted, however, that it is challenging to arrange ultraviolet LED 218 and blue LED 216 to illuminate fluorescence sample 204 directly, as illustrated in FIG. 2, for such small object distances, e.g., 5 mm or 10 mm. To address this challenge, an optical element, which in one example is a truncated pyramid having two parallel planes, can be used for refracting the illuminating light from the ultraviolet LED and the blue LED. In one example, an optical element such as truncated pyramid 302 is illustrated in FIG. 3 in accordance with the teachings of the present invention. In operation, a light source, such as for example the ultraviolet LED and/or the blue LED is adapted to emit light in a first direction towards the optical element. The optical element is optically coupled to receive the light through a side surface and refract the light to redirect the light in a second direction towards the fluorescence sample to illuminate fluorescence sample 204. Thus, truncated pyramid 302 bends light 304 emitted by blue LED 216 and light 306 emitted by ultraviolet LED 218 toward fluorescence sample 204 through the face of truncated pyramid 302 facing the sample 204 to illuminate fluorescence sample 204. In the example illustrated in FIG. 3, excitation filters 222 and 220 are optionally provided to filter the excitation light emitted by ultraviolet LED 218 and blue LED 216, respectively. Truncated pyramid 302 may be made from glass or other transparent materials to refract the light emitted from the ultraviolet LED 218 and/or the blue LED 216.

In various examples, light emitted from the ultraviolet LED 218 and/or the blue LED 216 may be collimated (not shown), and may be diverging. In other examples, ultraviolet LED 218 and blue LED 216 may be replaced by other light sources such as for example, but not limited to, a green LED, an ultraviolet laser diode, a blue laser diode, a green laser diode, or the like.

As shown in the depicted example, fluorescence light 308, 310 emitted from sample 204 to lens 206 may not be affected by truncated pyramid 302, since fluorescence light 308, 310 pass through the two parallel surfaces (i.e., planes) of truncated pyramid 302. Thus, the image sensor is adapted to acquire the image of the fluorescence sample 204 through the surface (i.e., plane) of the truncated pyramid 302 that faces the fluorescence sample 204, through a surface (i.e., plane) of the truncated pyramid 302 that faces the lens 206, and through the lens of the fluorescence imaging module. Sample 204 will appear closer to lens 206 as illustrated in detail in FIG. 4, in accordance with the teachings of the present invention. FIG. 5 illustrates in detail light 304 from blue LED 216 is bent toward the central area of sample 204, in accordance with the teachings of the present invention.

Figure 6A:
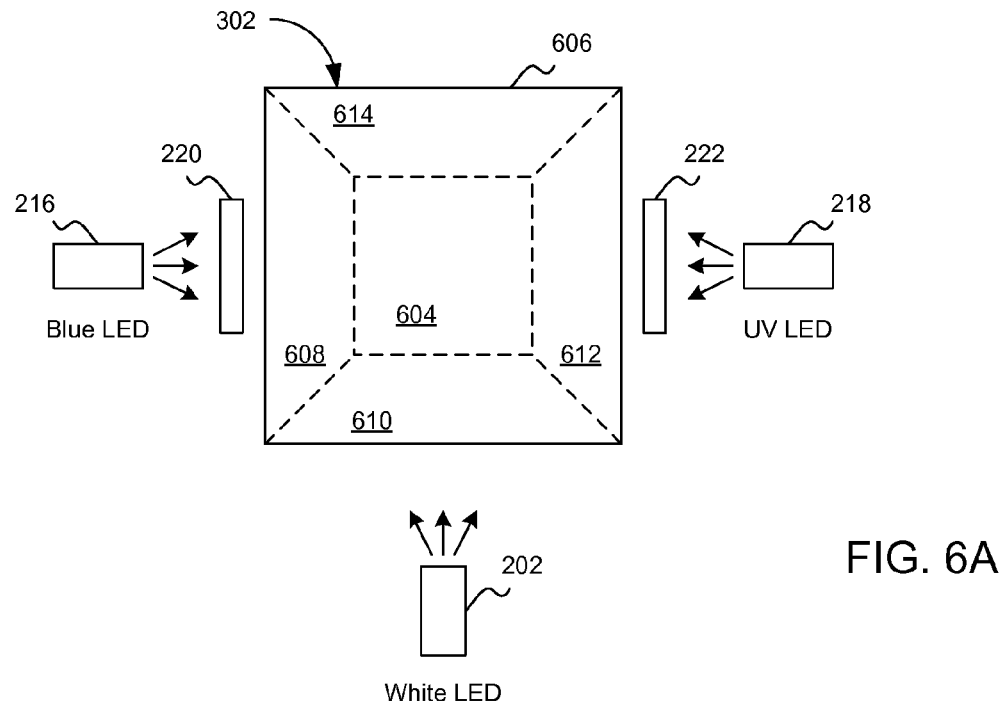
FIG. 6A shows a truncated pyramid having a square base and a square top in accordance with the teachings of the present invention.

FIG. 6A shows an example optical element that is a truncated pyramid 302 having a square base 604 and a square top 606 in accordance with the teachings of the present invention. Slanted side surfaces 608, 610, 612, and 614 connect square base 604 and square top 606. Light emitted from blue LED 216 enters from slanted side surface 608 and emerges at top square 606, which faces sample 204, and illuminates the central region of sample 204 (not shown). Light emitted from ultraviolet LED 218 enters from slanted side surface 612 and emerges at top square 606, and illuminates the central region of sample 204 (not shown). Excitation filters 222 and 220 are optionally provided to filter the excitation light emitted by ultraviolet LED 218 and blue LED 216, respectively. White LED 202 may be disposed on the side of truncated pyramid 302. For example, light emitted from white LED 202 enters from slanted side surface 610 and emerges at top square 606, and illuminates the central region of sample 204 (not shown). Slanted side surface 614 may be illuminated by a second white LED or light source having an other excitation wavelength, e.g., green LED or green laser diode. White LED 202 may be replaced by other white light sources. In this manner, white LED 202 in FIG. 2 is moved to the position under sample 204, thus the total length of the fluorescence imaging module can be further shortened in accordance with the teachings of the present invention.

Figure 6B:
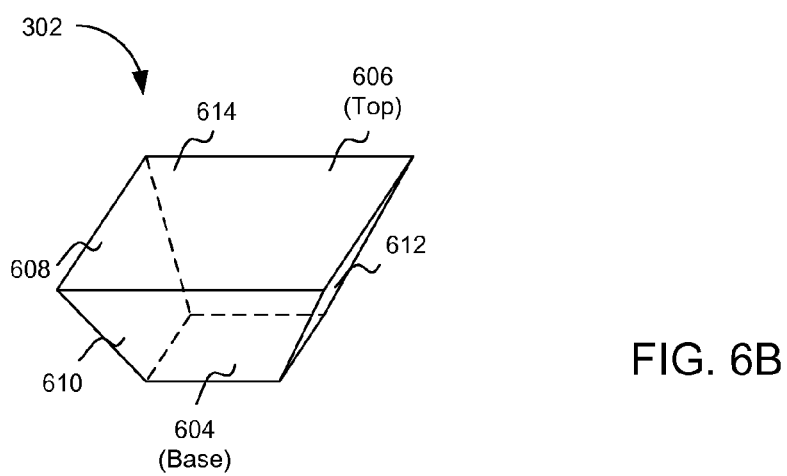
FIG. 6B shows truncated pyramid of FIG. 6A in perspective view in accordance with the teachings of the present invention.

FIG. 6B illustrates example truncated pyramid 302 in perspective view in accordance with the teachings of the present invention. Truncated pyramid 302 may have polygonal base and polygonal top to accommodate a plurality of LEDs or light sources.

Figure 7A:
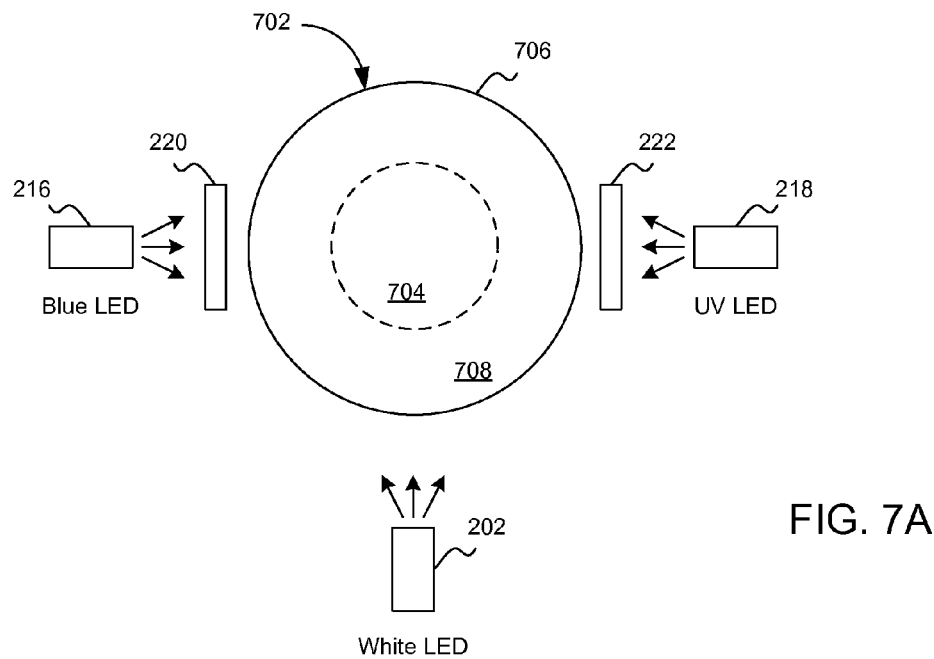
FIG. 7A shows a truncated cone having a circular base and a circular top in accordance with the teachings of the present invention.

FIG. 7A shows an example optical element that is a truncated cone 702 replacing truncated pyramid 302 of FIG. 6A, in accordance with the teachings of the present invention. Truncated cone 702 has a circular base 704 and a circular top 706. Circular base 704 and circular top 706 are connected by a lateral side surface 708. Similar to truncated pyramid 302, light emitted from blue LED 216, ultraviolet LED 218, and white LED 202 are directed toward lateral side surface 708 and emerge at circular top 706, which faces sample 204, to illuminate the central region of sample 204 (not shown).

Figure 7B:
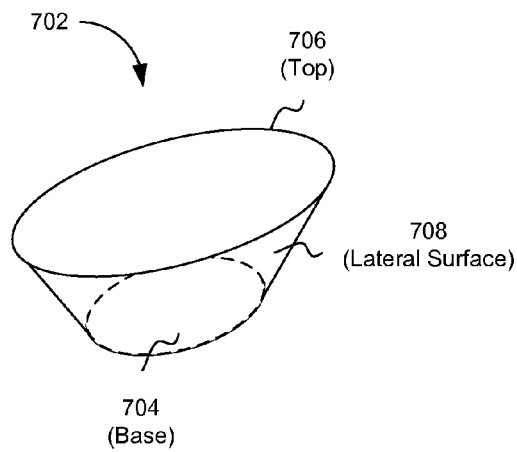
FIG. 7B shows truncated cone of FIG. 7A in perspective view in accordance with the teachings of the present invention.

Truncated cone 702 may be made from glass or other transparent materials. FIG. 7B illustrates truncated cone 702 in perspective view in accordance with the teachings of the present invention.

Figure 8:
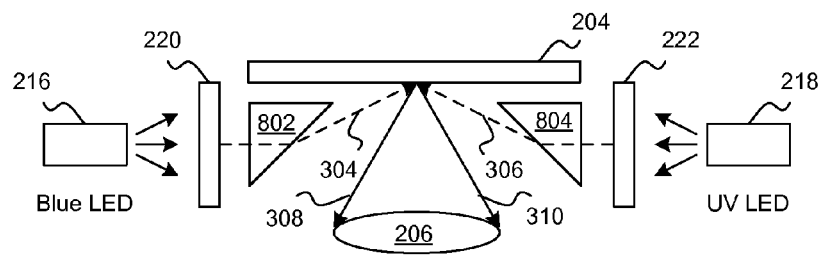
FIG. 8 shows an illuminating device comprising a set of prisms is used to bend light to illuminate sample in accordance with the teachings of the present invention.

FIG. 8 illustrates an example optical element that includes a set of prisms that is used to bend light from LEDs to illuminate sample 204 in accordance with the teachings of the present invention. Prisms may be made from glass or other transparent materials. In the example, a prism 802 is coupled to receive excitation light from blue LED 216 through a side surface. Prism 802 refracts the excitation light from blue LED 216 to illuminate sample 204 as shown. Similarly prism 804 receives excitation light from ultraviolet LED 218 through a side surface and refracts excitation light from ultraviolet LED 218 to illuminate sample 204 as shown. In the example, the refracted light illuminates the central region of sample 204. Excitation filters 222 and 220 are optionally provided to filter the excitation light emitted by ultraviolet LED 218 and blue LED 216, respectively. Light emitted from ultraviolet LED 218 and blue LED 216 may be collimated (not shown), and may be diverging. On the other hand, fluorescence light 308, 310 emitted from sample 204 to lens 206 may not be affected, since fluorescence light 308, 310 pass through an opening in the optical element not covered by any prism.

Figure 9:
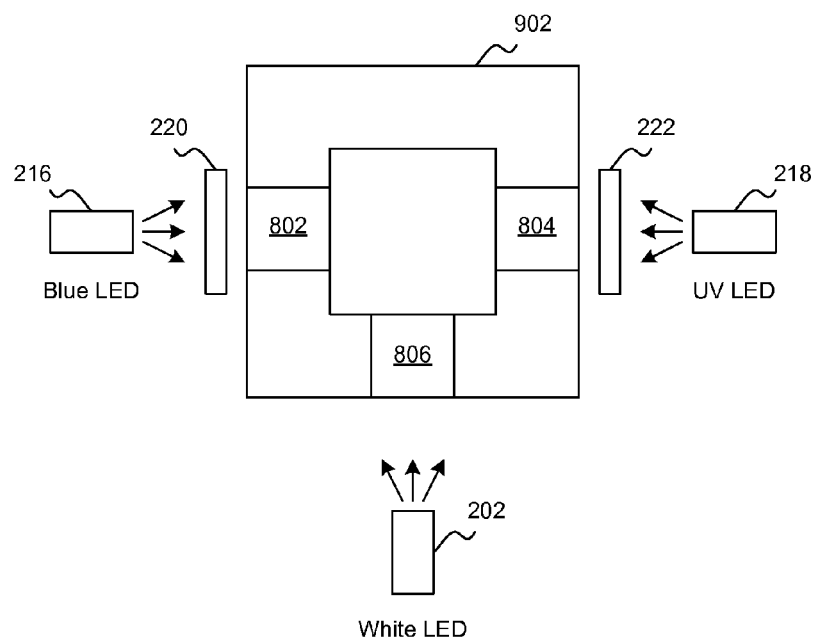
FIG. 9 illustrates a frame mounting individual prisms for bending light in accordance with the teachings of the present invention.

FIG. 9 illustrates a frame 902 mounting individual prisms 802, 804, and 806 of the optical element in accordance with the teachings of the present invention. Prism 806 may be used for refracting illuminating light from white LED 202. Prisms 802 and 804 are used for refracting excitation light from blue LED 216 and ultraviolet LED 218, respectively. It is appreciated that frame 902 may include a plurality of individual prisms for bending and directing light from a plurality of light sources to sample 204 (not shown). Frame 902 may be square, circular, polygonal, or of any shape.

Figure 10:
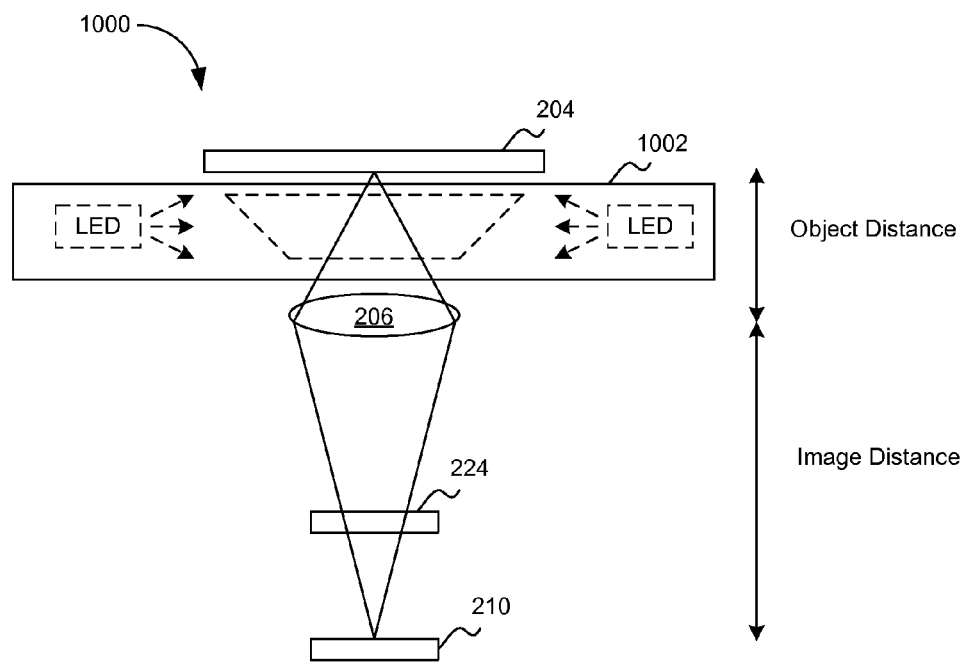
FIG. 10 shows an example fluorescence imaging module using an illuminating device in accordance with the teachings of the present invention.

FIG. 10 illustrates an example fluorescence imaging module 1000 using an illuminating device 1002 in accordance with the teachings of the present invention. Illuminating device 1002 may include an optical element such as example truncated pyramid 302 as shown in FIG. 3, a truncated cone 702 as shown in FIG. 7A, or a frame 902 mounting individual prisms as shown in FIG. 9. Illuminating device 1002 also comprises blue LED 216, ultraviolet LED 218, and white LED 202 as depicted in FIGS. 3-9. Illuminating device 1002 may include a plurality of LEDs or light sources. Illuminating device 1002 includes at least one LED or any light source including diode laser that emits excitation light.

Fluorescence imaging module 1000 further comprises a fluorescence sample 204, a lens 206, an emission filter 224, and an image sensor 210. Illuminating device 1002 is disposed between fluorescence sample 204 and lens 206. In this manner, the emitted fluorescence light from sample 204 is transmitted through emission filter 224. Lens 206 forms the fluorescence image of fluorescence sample 204 on image sensor 210. In one example, emission filter 224 is removable. In another example, emission filter 224 is interchangable with another emission filter for another emission wavelength.

Figure 11:
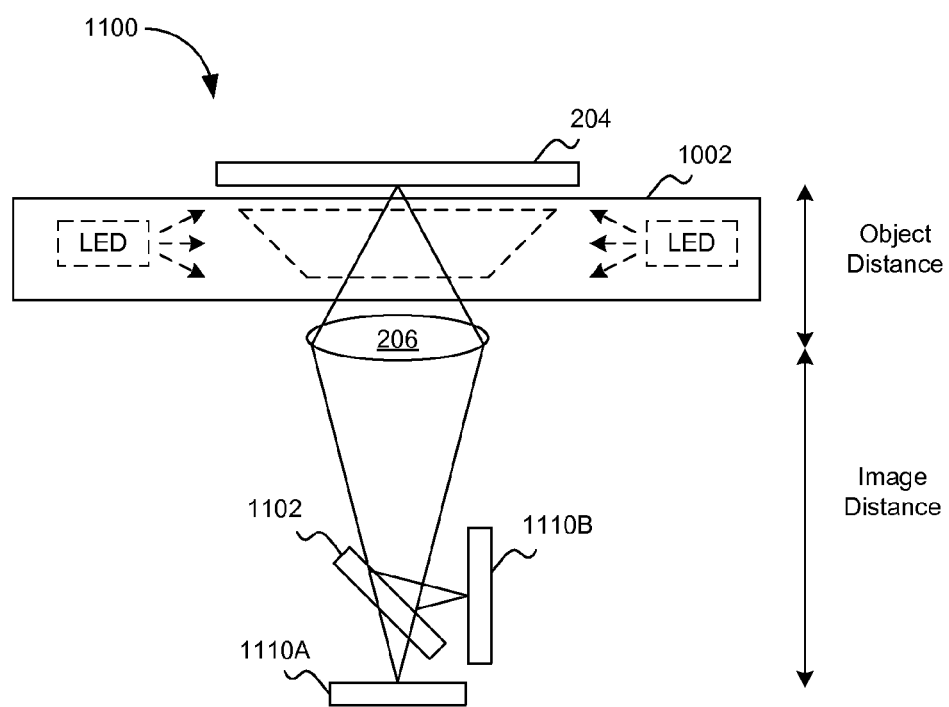
FIG. 11 shows an example fluorescence imaging module using an illuminating device and comprising two image sensors in accordance with the teachings of the present invention.

FIG. 11 illustrates a fluorescence imaging module 1100 using illuminating device 1002 in accordance with the teachings of the present invention. FIG. 11 differs from FIG. 10 in that a dichroic minor 1102 replaces emission filter 224. Light having emission wavelength is transmitted through dichroic minor 1102 arriving at an image sensor 1110A. Light having wavelengths other than emission wavelength is reflected by dichroic mirror 1102 arriving at an image sensor 1110B. In this manner, the fluorescence image, which is in emission wavelength, is formed by lens 206 on image sensor 1110A, while non-fluorescence image, which is in wavelengths other than the emission wavelength, will be formed by lens 206 on image sensor 1110B. Under white light illumination, without excitation light from the ultraviolet LED and the blue LED, the white light image of sample 204 can be obtained as the sum of image formed on image sensor 1110A and image formed on image sensor 1110B. In practice, without excitation light from the ultraviolet LED and the blue LED, the image formed at image sensor 1110A may be weak as compared with the image formed at image sensor 1110B. In one example, dichroic minor 1102 is interchangeable with another dichroic mirror for another emission wavelength.

It is appreciated that lens 206 in fluorescence imaging modules 1000 and 1100 may be an auto-focused lens, which is actuated by a voice coil motor (VCM) or other actuators. The actuator may be controlled by an algorithm based on the content of the scene detected, e.g., sharpness of image, or a sensor that calculates the object distance, or other means. Lens 206 may be a lens that has extended depth of field such that fine focusing is not necessary.

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention.

These modifications can be made to examples of the invention in light of the above detailed description. The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. A fluorescence imaging module, comprising:
   an image sensor;
   a lens disposed between a fluorescence sample and the image sensor to focus a fluorescence image of the fluorescence sample onto the image sensor, wherein the fluorescence sample is to be positioned an object distance away from the lens and wherein the lens is positioned an image distance away from the image sensor, wherein the image distance is greater than the object distance; and
   an illuminating device disposed between the fluorescence sample and the lens, wherein the illuminating device includes a light source and an optical element, wherein the light source is adapted to emit light in a first direction towards the optical element and wherein the optical element is optically coupled to receive the light and redirect the light in a second direction towards the fluorescence sample to illuminate the fluorescence sample.

2. The fluorescence imaging module of claim 1 wherein the optical element includes a first surface optically coupled to receive the light in the first direction from the light source, wherein the optical element is adapted to refract the light to redirect the light in the second direction towards the fluorescence sample through a second surface of the optical element to illuminate the fluorescence sample.

3. The fluorescence imaging module of claim 1 wherein the light source is a first light source of a plurality of light sources included in the illuminating device, wherein each one of the plurality of light sources is adapted to emit light that is optically coupled to be received by the optical element, and wherein the optical element is adapted to refract the respective light received from each one of the plurality of light sources towards the fluorescence sample to illuminate the fluorescence sample.

4. The fluorescence imaging module of claim 3 wherein the optical element comprises a truncated pyramid disposed between the fluorescence sample and the lens, wherein each one of the plurality of light sources is adapted to emit light that is optically coupled to be received by a respective one of a plurality of side surfaces of the truncated pyramid, and wherein the truncated pyramid is adapted to refract the respective light received from each one of the plurality of light sources and redirect the respective light received from each one of the plurality of light sources towards the fluorescence sample through a surface of the truncated pyramid that faces the fluorescence sample to illuminate the fluorescence sample.

5. The fluorescence imaging module of claim 4 wherein the image sensor is adapted to acquire the fluorescence image of the fluorescence sample through the surface of the truncated pyramid that faces the fluorescence sample, through a surface of the truncated pyramid that faces the lens, and through the lens.

6. The fluorescence imaging module of claim 3 wherein the optical element comprises a truncated cone disposed between the fluorescence sample and the lens, wherein each one of the plurality of light sources is adapted to emit light that is optically coupled to be received by a side surface of the truncated cone, and wherein the truncated cone is adapted to refract the respective light received from each one of the plurality of light sources and redirect the respective light received from each one of the plurality of light sources towards the fluorescence sample through a surface of the truncated cone that faces the fluorescence sample to illuminate the fluorescence sample.

7. The fluorescence imaging module of claim 6 wherein the image sensor is adapted to acquire the fluorescence image of the fluorescence sample through the surface of the truncated cone that faces the fluorescence sample, through a surface of the truncated cone that faces the lens, and through the lens.

8. The fluorescence imaging module of claim 3 wherein the optical element comprises a plurality of prisms arranged between the fluorescence sample and the lens, wherein each one of the plurality of light sources is adapted to emit light that is optically coupled to be received by a first surface of a respective one of the plurality prisms, and wherein each respective one of the plurality of prisms is adapted to refract the light received from the respective one of the plurality of light sources and redirect the light received from the respective one of the plurality of light sources towards the fluorescence sample through a second surface of the respective one of the plurality of prisms to illuminate the fluorescence sample.

9. The fluorescence imaging module of claim 1 further comprising an emission filter disposed between the fluorescence sample and the lens to transmit light having an emission wavelength, wherein the image sensor is adapted to acquire the fluorescence image of the fluorescence sample through the lens and through the emission filter.

10. The fluorescence imaging module of claim 9, wherein the emission filter is removable.

11. The fluorescence imaging module of claim 9, wherein the emission filter is interchangeable.

12. The fluorescence imaging module of claim 1 further comprising:
   a dichroic mirror disposed between the lens and the image sensor, wherein the dichroic minor is adapted to transmit light having an emission wavelength and reflect light having wavelengths other than the emission wavelength, wherein the image sensor is adapted to acquire the fluorescence image of the fluorescence sample through the lens and through the dichroic mirror; and a second image sensor optically coupled to receive the light reflected from the dichroic minor having wavelengths other than the emission wavelength, wherein the second image sensor is adapted to acquire a non-fluorescence image of the fluorescence sample through the lens and from the dichroic minor.

13. The fluorescence imaging module of claim 12, wherein the dichroic mirror is interchangeable.

14. The fluorescence imaging module of claim 12 wherein a white light image of the fluorescence sample is obtained by summing the fluorescence image acquired by the image sensor and the non-fluorescence image acquired by the second image sensor.

15. The fluorescence imaging module of claim 1 wherein the light source comprises one of an ultraviolet LED, a blue LED, a green LED, an ultraviolet laser diode, a blue laser diode, and a green laser diode.

16. The fluorescence imaging module of claim 3 wherein the plurality of light source comprise at least one of a white LED, an ultraviolet LED, a blue LED, a green LED, an ultraviolet laser diode, a blue laser diode, and a green laser diode.

17. The fluorescence imaging module of claim 1 wherein the lens comprises an auto-focused lens.

18. The fluorescence imaging module of claim 1 wherein the lens is included in a lens system.

19. The fluorescence imaging module of claim 1 wherein a magnification of the fluorescence image of the fluorescence sample is substantially equal to a ratio of the image distance to the object distance.

20. A fluorescence imaging module, comprising:
an image sensor;
a lens disposed between a fluorescence sample and the image sensor to focus a fluorescence image of the fluorescence sample onto the image sensor, wherein the fluorescence sample is to be positioned an object distance away from the lens and wherein the lens is positioned an image distance away from the image sensor, wherein a total distance of the fluorescence sample to the image sensor is substantially equal to a sum of the image distance and the object distance; and
an illuminating device disposed between the fluorescence sample and the lens, wherein the illuminating device includes a light source and an optical element, wherein the light source is adapted to emit light in a first direction towards the optical element and wherein the optical element is optically coupled to receive the light and redirect the light in a second direction towards the fluorescence sample to illuminate the fluorescence sample.

21. The fluorescence imaging module of claim 20 wherein the optical element includes a first surface optically coupled to receive the light in the first direction from the light source, wherein the optical element is adapted to refract the light to redirect the light in the second direction towards the fluorescence sample through a second surface of the optical element to illuminate the fluorescence sample.

22. The fluorescence imaging module of claim 20 wherein the light source is a first light source of a plurality of light sources included in the illuminating device, wherein each one of the plurality of light sources is adapted to emit light that is optically coupled to be received by the optical element, and wherein the optical element is adapted to refract the respective light received from each one of the plurality of light sources towards the fluorescence sample to illuminate the fluorescence sample.

23. The fluorescence imaging module of claim 22 wherein the optical element comprises a truncated pyramid disposed between the fluorescence sample and the lens, wherein each one of the plurality of light sources is adapted to emit light that is optically coupled to be received by a respective one of a plurality of side surfaces of the truncated pyramid, and wherein the truncated pyramid is adapted to refract the respective light received from each one of the plurality of light sources and redirect the respective light received from each one of the plurality of light sources towards the fluorescence sample through a surface of the truncated pyramid that faces the fluorescence sample to illuminate the fluorescence sample.

24. The fluorescence imaging module of claim 22 wherein the optical element comprises a truncated cone disposed between the fluorescence sample and the lens, wherein each one of the plurality of light sources is adapted to emit light that is optically coupled to be received by a side surface of the truncated cone, and wherein the truncated cone is adapted to refract the respective light received from each one of the plurality of light sources and redirect the respective light received from each one of the plurality of light sources towards the fluorescence sample through a surface of the truncated cone that faces the fluorescence sample to illuminate the fluorescence sample.

25. The fluorescence imaging module of claim 22 wherein the optical element comprises a plurality of prisms arranged between the fluorescence sample and the lens, wherein each one of the plurality of light sources is adapted to emit light that is optically coupled to be received by a first surface of a respective one of the plurality prisms, and wherein each respective one of the plurality of prisms is adapted to refract the light received from the respective one of the plurality of light sources and redirect the light received from the respective one of the plurality of light sources towards the fluorescence sample through a second surface of the respective one of the plurality of prisms to illuminate the fluorescence sample.

26. The fluorescence imaging module of claim 20 wherein a magnification of the fluorescence image of the fluorescence sample is substantially equal to the ratio of the image distance to the object distance.

* * * * *